(12) United States Patent
Ohtsuka et al.

(10) Patent No.: US 7,449,709 B2
(45) Date of Patent: Nov. 11, 2008

(54) APPARATUS FOR AND METHOD OF READING AND ERASING RADIATION IMAGE INFORMATION

(75) Inventors: Yuzuru Ohtsuka, Minami-ashigara (JP); Masakazu Nakajo, Minami-ashigara (JP); Osamu Kuroda, Fujisawa (JP); Yoshihiro Ishikawa, Kanagawa-ken (JP); Hideki Suzuki, Kanagawa-ken (JP); Yasunori Ohta, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 224 days.

(21) Appl. No.: 11/227,165

(22) Filed: Sep. 16, 2005

(65) Prior Publication Data

US 2006/0060804 A1  Mar. 23, 2006

(30) Foreign Application Priority Data

Sep. 17, 2004  (JP)  ............................. 2004-272446
Jul. 13, 2005  (JP)  ............................. 2005-204344

(51) Int. Cl.
   *B65H 5/00*  (2006.01)
(52) U.S. Cl. .................. 250/589; 250/580; 250/581
(58) Field of Classification Search ................ 250/581, 250/582, 583, 584, 585, 586, 587, 588, 589, 250/590, 591
See application file for complete search history.

(56) References Cited

U.S. PATENT DOCUMENTS

| | | | | |
|---|---|---|---|---|
| 5,340,995 A | * | 8/1994 | Verbeke et al. | 250/581 |
| 5,818,065 A | * | 10/1998 | Exelmans | 250/588 |
| 6,342,708 B1 | * | 1/2002 | Iiyama et al. | 250/589 |
| 7,138,647 B2 | * | 11/2006 | Nakajo | 250/588 |
| 2004/0169152 A1 | * | 9/2004 | Tsutoh et al. | 250/589 |
| 2006/0060805 A1 | * | 3/2006 | Ohtsuka et al. | 250/589 |

FOREIGN PATENT DOCUMENTS

JP   2002-156716 A   5/2002

\* cited by examiner

*Primary Examiner*—Christine Sung
(74) *Attorney, Agent, or Firm*—Sughrue Mion, PLLC (57) ABSTRACT

A cassette is delivered from a cassette loader through a stock unit to a releasing unit. After a stimulable phosphor panel is supplied from the cassette to a reading unit by an unlocking mechanism and a panel ejecting mechanism, the cassette is fed to a position below an erasing unit so as to wait for the stimulable phosphor panel. After recorded radiation image information is read from the stimulable phosphor panel by the reading unit, the stimulable phosphor panel is fed to the erasing unit, which erases remaining radiation image information from the stimulable phosphor panel. Thereafter, the stimulable phosphor panel is stored back into the waiting cassette, which is delivered to a cassette discharger.

10 Claims, 5 Drawing Sheets

APPARATUS FOR AND METHOD OF READING AND ERASING RADIATION IMAGE INFORMATION

BACKGROUND OF THE INVENTION

1. Field of the Invention

The present invention relates to an apparatus for and a method of reading radiation image information recorded in a stimulable phosphor panel that is stored in a cassette, thereafter erasing remaining radiation image information from the stimulable phosphor panel, and discharging the stimulable phosphor panel.

2. Description of the Related Art

There has heretofore been known a radiation image information reading and erasing apparatus employing a stimulable phosphor panel which, when exposed to an applied radiation, stores part of the energy of the radiation, and, when subsequently exposed to applied stimulating rays such as visible light, emits light in proportion to the stored energy of the radiation.

The radiation image information reading and erasing apparatus includes a cassette loader for loading a plurality of cassettes each storing a stimulable phosphor panel which records therein radiation image information of a subject such as a human body, a reading unit for applying stimulating light to the stimulable phosphor panel removed from one of the cassettes to read the radiation image information from the stimulable phosphor panel, an erasing unit for applying erasing light to the stimulable phosphor panel from which the radiation image information has been read to erase remaining radiation image information from the stimulable phosphor panel, and a cassette discharger for discharging the stimulable phosphor panel stored in the cassette after the remaining radiation image information has been erased from the stimulable phosphor panel.

Japanese Laid-Open Patent Publication No. 2002-156716 discloses a radiation image reading apparatus. The disclosed radiation image reading apparatus operates as follows. A cassette storing a stimulable phosphor sheet is introduced from a cassette insertion slot into an apparatus housing, and thereafter the stimulable phosphor sheet is removed from the cassette and supplied to a reading unit and an erasing unit. After the stimulable phosphor sheet is processed by the reading unit and the erasing unit, the stimulable phosphor sheet is put back into the cassette that is remaining in the same location in the apparatus housing, and then the cassette holding the stimulable phosphor sheet therein is discharged out of the apparatus housing through a cassette discharge slot.

In the disclosed radiation image reading apparatus, the cassette introduced into the apparatus housing remains in the same location until the processing of the stimulable phosphor sheet with the reading unit and the erasing unit is completed. Since the cassette stays in the apparatus housing, the next cassette cannot be introduced into the apparatus housing. Therefore, the disclosed radiation image reading apparatus is disadvantageous in that it is unable to process a plurality of cassettes efficiently at the same time.

SUMMARY OF THE INVENTION

It is a general object of the present invention to provide an apparatus for and a method of efficiently reading and erasing radiation image information recorded in a stimulable phosphor panel that is stored in a cassette.

A major object of the present invention is to provide an apparatus for and a method of efficiently reading and erasing radiation image information recorded in a plurality of stimulable phosphor panels that are stored in respective cassettes which are retained in a cassette loader.

Another major object of the present invention is to provide an apparatus for and a method of reading and erasing radiation image information concurrently from a plurality of stimulable phosphor panels.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
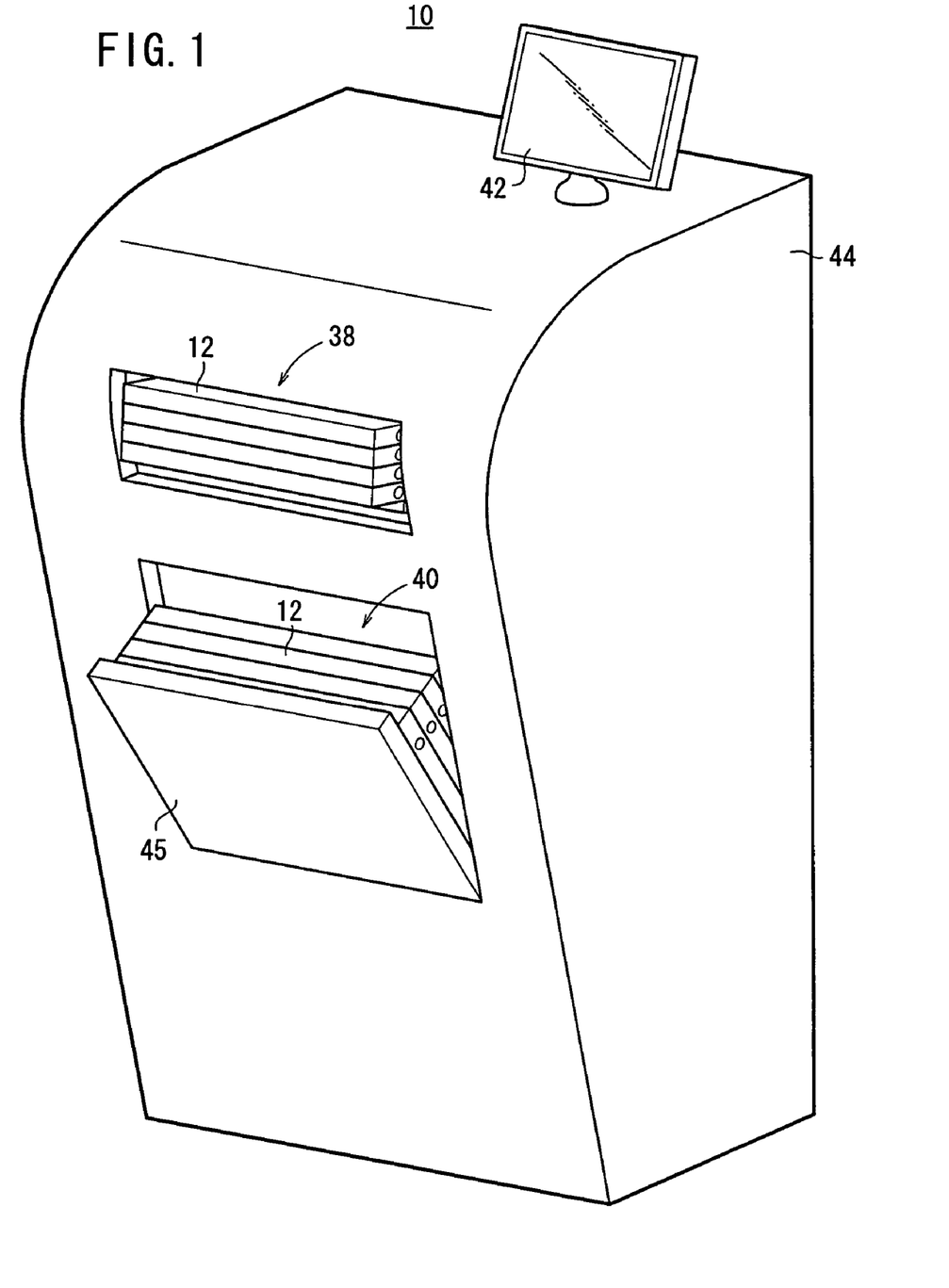
FIG. 1 is a perspective view of a radiation image information reading and erasing apparatus according to the present invention.

FIG. 1 shows in perspective a radiation image information reading and erasing apparatus 10 according to the present invention.

The radiation image information reading and erasing apparatus 10 basically operates as follows. A stimulable phosphor panel 14 (see FIG. 2) is removed from a cassette 12. Radiation image information recorded in the stimulable phosphor panel 14 is read from the stimulable phosphor panel 14, and then remaining radiation image information is erased from the stimulable phosphor panel 14. Thereafter, the stimulable phosphor panel 14 is put back into the cassette 12, which is discharged from the radiation image information reading and erasing apparatus 10.

Figure 2:
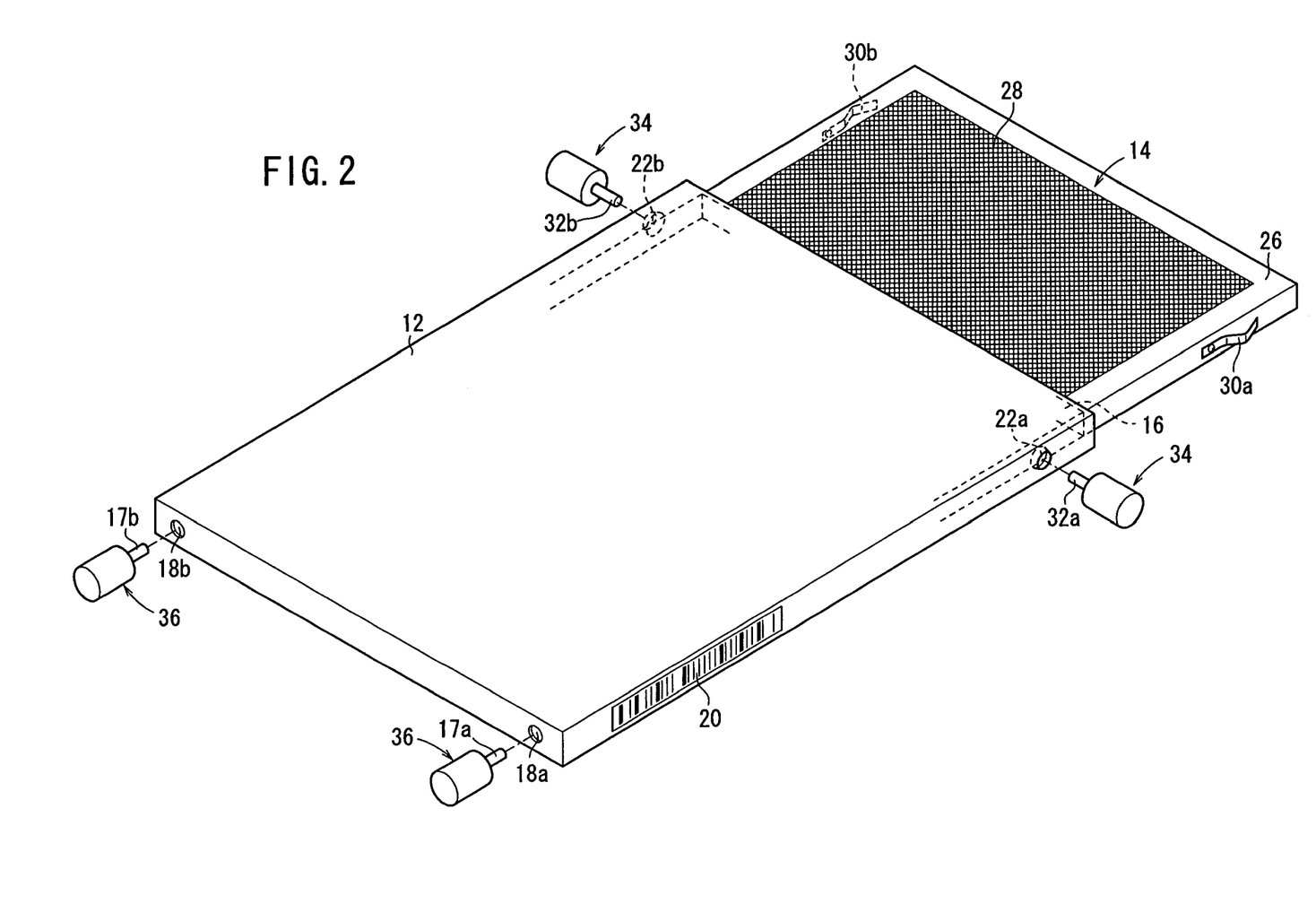
FIG. 2 is a perspective view of a cassette and a stimulable phosphor panel for use in the radiation image information reading and erasing apparatus according to the present invention.

As shown in FIG. 2, the cassette 12 has an opening 16 defined in an end thereof for inserting and removing the stimulable phosphor panel 14 therethrough into and out from the cassette 12. The cassette 12 also has insertion holes 18a, 18b defined in an opposite end thereof at spaced locations for inserting ejecting pins 17a, 17b respectively therethrough to remove the stimulable phosphor panel 14 through the opening 16 from the cassette 12. An identification strip 20 such as a bar code or the like which represents identification information for specifying the size of the cassette 12 and the stimulable phosphor panel 14 stored in the cassette 12 is applied to one of the side surfaces of the cassette 12. The cassette 12 also has retaining holes 22a, 22b defined respectively in opposite side walls of the cassette 12 near the opening 16 for retaining the stimulable phosphor panel 14 in the cassette 12.

The stimulable phosphor panel 14 stored in the cassette 12 comprises a hard panel having a columnar stimulable phosphor layer 28 evaporated on a support board 26 which is made of a light-permeable hard material such as glass or the like. The columnar stimulable phosphor layer 28 may be formed by any of various processes including a vacuum evaporation process in which a stimulable phosphor is heated and evaporated in a vacuum container and then deposited on the support board 26, a sputtering process, a CVD process, and an ion plating process. The columnar stimulable phosphor layer 28 has the stimulable phosphor formed as optically independent columns substantially perpendicular to the plane of the stimulable phosphor panel 14. The columnar stimulable phosphor layer 28 is highly sensitive to a radiation applied thereto, lowers the granularity of images recorded therein, and reduces the scattering of stimulating light applied thereto for producing sharp images.

Retainer leaf springs 30a, 30b are mounted respectively on opposite side surfaces of the stimulable phosphor panel 14 near one end thereof. When the stimulable phosphor panel 14 is inserted into the cassette 12, the retainer leaf springs 30a, 30b engage in the respective retaining holes 22a, 22b, thereby securing and retaining the stimulable phosphor panel 14 in the cassette 12. The stimulable phosphor panel 14 can be released from the cassette 12 when unlocking pins 32a, 32b are inserted respectively into the retaining holes 22a, 22b to push the retainer leaf springs 30a, 30b out of the respective retaining holes 22a, 22b.

The radiation image information reading and erasing apparatus 10 has a cassette loader 38 for loading a plurality of cassettes 12 therein, a cassette discharger 40 for discharging a plurality of cassettes 12 that have been processed by the radiation image information reading and erasing apparatus 10, and a control display panel 42 for displaying information concerning the processing operation of the radiation image information reading and erasing apparatus 10.

The cassette loader 38 is disposed substantially centrally in a front wall of a housing 44 of the radiation image information reading and erasing apparatus 10. The cassette loader 38 is capable of loading a plurality of vertically stacked cassettes 12 therein. The cassette discharger 40 is disposed in the front wall of the housing 44 below the cassette loader 38, and stocks a plurality of erected cassettes 12 therein. The cassette discharger 40 has an openable and closable lid 45 pivoted at its lower end. When the lid 45 is pulled out about its pivoted lower end, the cassettes 12 in the cassette discharger 40 can manually be removed from the cassette discharger 40.

Figure 3:
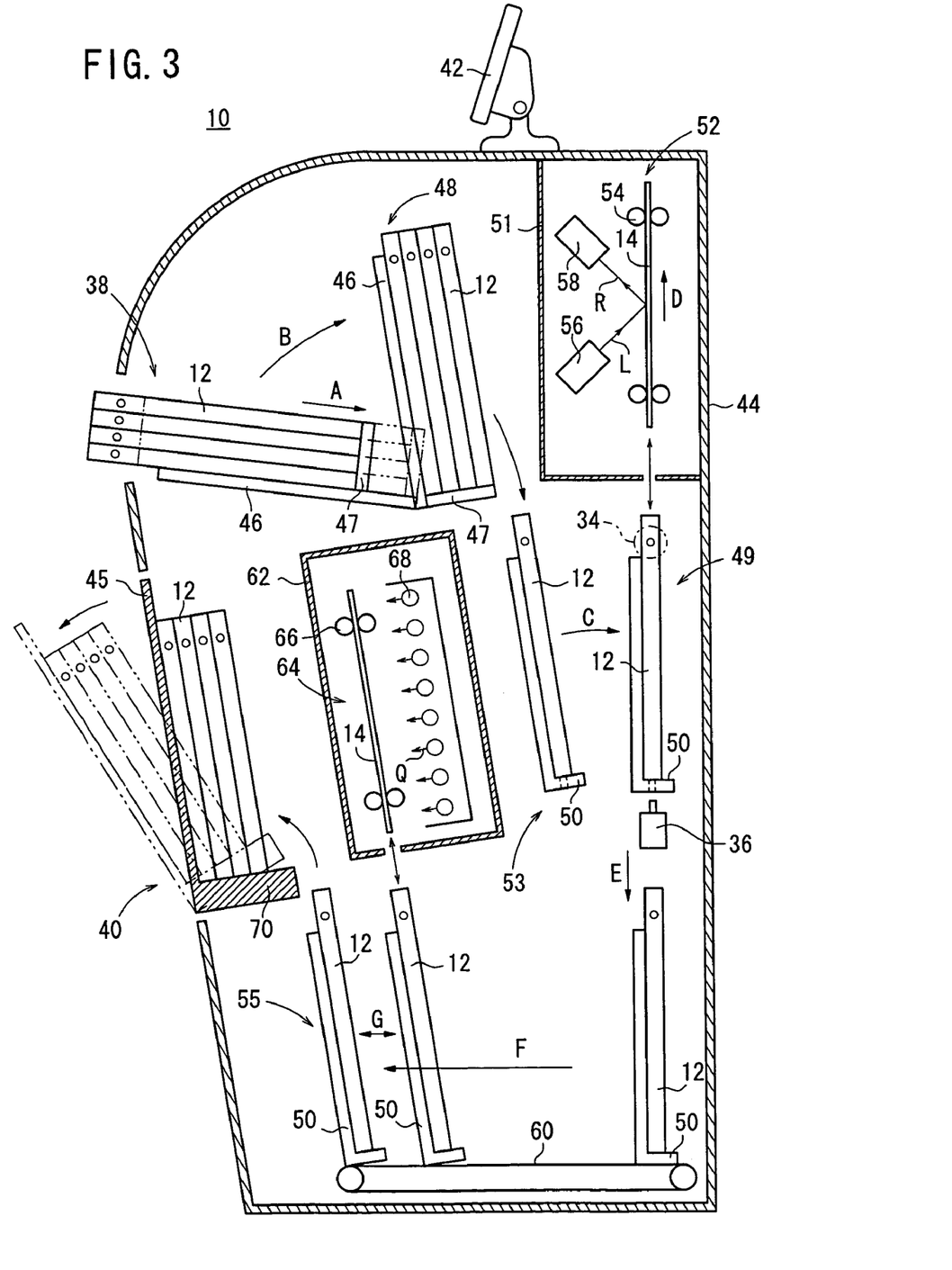
FIG. 3 is a schematic vertical cross-sectional view of the radiation image information reading and erasing apparatus according to the present invention.

FIG. 3 shows internal structural details of the radiation image information reading and erasing apparatus 10.

As shown in FIG. 3, the cassette loader 38 has a stack table 46 for supporting a stack of cassettes 12 thereon. A displacement plate 47 which is displaceable in the direction indicated by the arrow A is disposed on the stack table 46. The cassettes 12 that are placed on the stack table 46 are inserted together with the displacement plate 47 along the stack table 46 into the housing 44. The stack table 46 is angularly movable about an inner end thereof in the direction indicated by the arrow B for supplying the stacked cassettes 12 loaded in the cassette loader 38 in a substantially erected state into a stock unit 48.

The stock unit 48 is positioned above a first waiting unit 53 having a holder 50 for holding a cassette 12 that is supplied from the stock unit 48. The holder 50 is angularly movable from the first waiting unit 53 in the direction indicated by the arrow C, or is movable in a substantially horizontal direction into a releasing unit 49 (first panel supply mechanism). The releasing unit 49 has an unlocking mechanism 34 disposed in an upper area thereof and having the unlocking pins 32a, 32b for unlocking the stimulable phosphor panel 14 retained in the cassette 12. The releasing unit 49 also has a panel ejecting mechanism 36 disposed in a lower area thereof and having the ejecting pins 17a, 17b for ejecting the stimulable phosphor panel 14 from the cassette 12.

The releasing unit 49 is disposed beneath a reading unit 52 that is shielded against entry of light by a partition wall 51. The reading unit 52 comprises a panel feed mechanism 54 for gripping and feeding the stimulable phosphor panel 14 removed from the cassette 12 in a vertically upward direction, i.e., in the auxiliary scanning direction indicated by the arrow D, a stimulating light scanner 56 for applying stimulating light L in the form of a laser beam to the stimulable phosphor panel 14 fed by the panel feed mechanism 54 while the stimulating light L is being applied in a main scanning direction perpendicular to the auxiliary scanning direction, and a photoelectric transducer 58 such as a photomultiplier, a CCD line sensor, or the like for converting light R which is emitted from the stimulable phosphor panel 14 that is irradiated with the stimulating light L, into an electric signal.

The holder 50 is movable downwardly in the direction indicated by the arrow E while holding the cassette 12 or the stimulable phosphor panel 14. At the lower end of the holder 50 after moving downwardly in the direction indicated by the arrow E, there is disposed a conveyor 60 (feed mechanism) for feeding the cassette 12 or the stimulable phosphor panel 14 together with the holder 50 substantially horizontally in the direction indicated by the arrow F.

An erasing unit 64 that is shielded against entry of light by a partition wall 62 is disposed above a substantially central portion of the conveyor 60. The erasing unit 64 comprises a panel supply mechanism 66 (second panel supply mechanism) for holding a stimulable phosphor panel 14 which is supplied from the holder 50 on the conveyor 60 and discharging the stimulable phosphor panel 14 from the erasing unit 64 and inserting the discharged stimulable phosphor panel 14 into the cassette 12 on the conveyor 60, and a plurality of erasing light sources 68 such as halogen lamps, cold-cathode tubes, or the like for applying erasing light Q to the stimulable phosphor panel .14 to erase remaining radiation image information from the stimulable phosphor panel 14. Preferably, the partition wall 62 has inner surfaces capable of efficiently reflecting the erasing light Q, such as glossy metal surfaces that are coated.

A second waiting unit 55 is disposed on the terminal end of the conveyor 60 with respect to the direction indicated by the arrow F along which the cassette 12 is fed by the conveyor 60. The second waiting unit 55 is positioned beneath the cassette discharger 40. A stack table 70 for placing a plurality of cassettes 12 thereon is joined to the lower end of the lid 45 of the cassette discharger 40. The cassette discharger 40 stocks stimulable phosphor panels 14 from which remaining radiation image information has been erased, for a long period of time. Therefore, portions of the housing 44, the lid 45, and the stack table 70 which are disposed around the cassette discharger 40 are made of a heavy metal such as lead or the like to function as isolation walls for blocking radiations applied from outside of the radiation image information reading and erasing apparatus 10.

The radiation image information reading and erasing apparatus 10 has at least two holders 50 circulating from the first waiting unit 53 through the releasing unit 49 and the conveyor 60 to the second waiting unit 55. After each of the holders 50 has discharged the cassette 12 containing the stimulable phosphor panel 14 therein from the second waiting unit 55, it returns from the conveyor 60 to the first waiting unit 53.

The radiation image information reading and erasing apparatus 10 is basically constructed as described above. Operation of the radiation image information reading and erasing apparatus 10 will be described below.

The operator loads a cassette 12 storing therein a stimulable phosphor panel 14 with radiation image information recorded therein into the cassette loader 38. The stack table 46 of the cassette loader 38 is capable of placing a plurality of stacked cassettes 12 thereon. Therefore, the operator can easily load a plurality of cassettes 12 simultaneously into the cassette loader 38.

After the cassettes 12 have been placed on the stack table 46, the displacement plate 47 is displaced in the direction indicated by the arrow A, bringing the cassettes 12 into the housing 44 of the radiation image information reading and erasing apparatus 10. Then, the stack table 46 is angularly moved in the direction indicated by the arrow B to place the cassettes 12 into the stock unit 48. At this time, a next batch of cassettes 12 may be loaded into the cassette loader 38.

One of the cassettes 12 stocked in the stock unit 48 is transferred onto the holder 50 in the first waiting unit 53 that is disposed below the stock unit 48. Thereafter, the cassette 12 is moved in the direction indicated by the arrow C by the holder 50 and placed together with the holder 50 into the releasing unit 49. After the cassette 12 has moved together with the holder 50 into the releasing unit 49, another holder 50 is placed in the first waiting unit 53 for receiving the next cassette 12 from the stock unit 48.

When the cassette 12 moves into the releasing unit 49, the unlocking mechanism 34 is actuated to insert the unlocking pins 32a, 32b respectively into the retaining holes 22a, 22b of the cassette 12, pushing the retainer leaf springs 30a, 30b to release the stimulable phosphor panel 14. The panel ejecting mechanism 36 is actuated to insert the ejecting pins 17a, 17b into the respective insertion holes 18a, 18b of the cassette 12, pushing the stimulable phosphor panel 14 out of the cassette 12 into the reading unit 52 which is positioned above the releasing unit 49.

The empty cassette 12 from which the stimulable phosphor panel 14 has been transferred to the reading unit 52 is immediately lowered by the holder 50 in the direction indicated by the arrow E and placed onto the conveyor 60. The empty cassette 12 is then fed by the conveyor 60 in the direction indicated by the arrow F to the second waiting unit 55 at the terminal end of the conveyor 60, where the empty cassette 12 waits to receive the stimulable phosphor panel 14.

In the reading unit 52, the stimulable phosphor panel 14 is gripped by the panel feed mechanism 54 and fed thereby in the vertically upward direction, i.e., in the auxiliary scanning direction indicated by the arrow D. While the stimulable phosphor panel 14 is being fed in the auxiliary scanning direction, it is irradiated with the stimulating light L which is emitted from the stimulating light scanner 56 and applied in the main scanning direction. The stimulable phosphor panel 14 emits light R representative of the recorded radiation image information upon exposure to the stimulating light L. The emitted light R is converted by the photoelectric transducer 58 into an electric signal representative of the recorded radiation image information.

The stimulable phosphor panel 14 from which the recorded radiation image information has been read is then quickly placed directly onto the holder 50, which is placed on the conveyor 60, without being inserted into the cassette 12. During this time, the next cassette 12 storing a stimulable phosphor panel 14 is introduced into the releasing unit 49 by another holder 50. In the releasing unit 49, the stimulable phosphor panel 14 is removed from the next cassette 12 and then delivered into the reading unit 52 for processing.

The stimulable phosphor panel 14 that has been placed on the conveyor 60 is fed by the conveyor 60 to a position beneath the erasing unit 64, and then supplied upwardly to the erasing unit 64. In the erasing unit 64, the erasing light Q emitted from the erasing light sources 68 is applied to the stimulable phosphor panel 14 held by the panel supply mechanism 66, erasing remaining radiation image information from the stimulable phosphor panel 14. During this time, the empty cassette 12 is supplied from the second waiting unit 55 at the terminal end of the conveyor 60 to the position beneath the erasing unit 64 in the direction indicated by the arrow G, and waits in that position.

The stimulable phosphor panel 14 from which the remaining radiation image information has been erased is delivered downwardly into the empty cassette 12 on the conveyor 60 by the panel supply mechanism 66. The cassette 12 with the stimulable phosphor panel 14 stored therein is moved to the second waiting unit 55 by the conveyor 60, and then placed onto the stack table 70 of the cassette discharger 40.

In the cassette discharger 40 which stocks a plurality of cassettes 12, since the lid 45 and the stack table 70 are made of a heavy metal such as lead or the like to function as isolation walls, the cassettes 12 in the cassette discharger 40 are kept in stock under good condition for a long period of time without being adversely affected by radiations applied from outside of the radiation image information reading and erasing apparatus 10.

When the operator pulls out the lid 45, the cassettes 12 which house the respective recordable stimulable phosphor panels 14 therein and are placed on the stack table 70 can be removed from the radiation image information reading and erasing apparatus 10. The recordable stimulable phosphor panels 14 in the cassettes 12 can be used again for recording radiation image information therein.

After the cassette 12 with the stimulable phosphor panel 14 stored therein has been transferred from the second waiting unit 55 to the cassette discharger 40, the empty holder 50 is returned from the conveyor 60 to the first waiting unit 53 for receiving the next cassette 12 from the stock unit 48.

In the above embodiment, a stimulable phosphor panel 14 is removed from a cassette 12 in the releasing unit 49. However, a stimulable phosphor panel 14 may be removed from a cassette 12 in the stock unit 48 or the first waiting unit 53 and supplied to the reading unit 52. In this case, the unlocking mechanism 34 and the panel ejecting mechanism 36 are provided in the stock unit 48 or the first waiting unit 53.

An empty cassette 12 from which the stimulable phosphor panel 14 has been removed below the erasing unit 64 may be temporarily placed in the cassette discharger 40. After remaining radiation image information has been erased from the stimulable phosphor panel 14, the empty cassette 12 may be delivered from the cassette discharger 40 to the position below the erasing unit 64 for receiving the stimulable phosphor panel 14 from the erasing unit 64.

Figure 4:
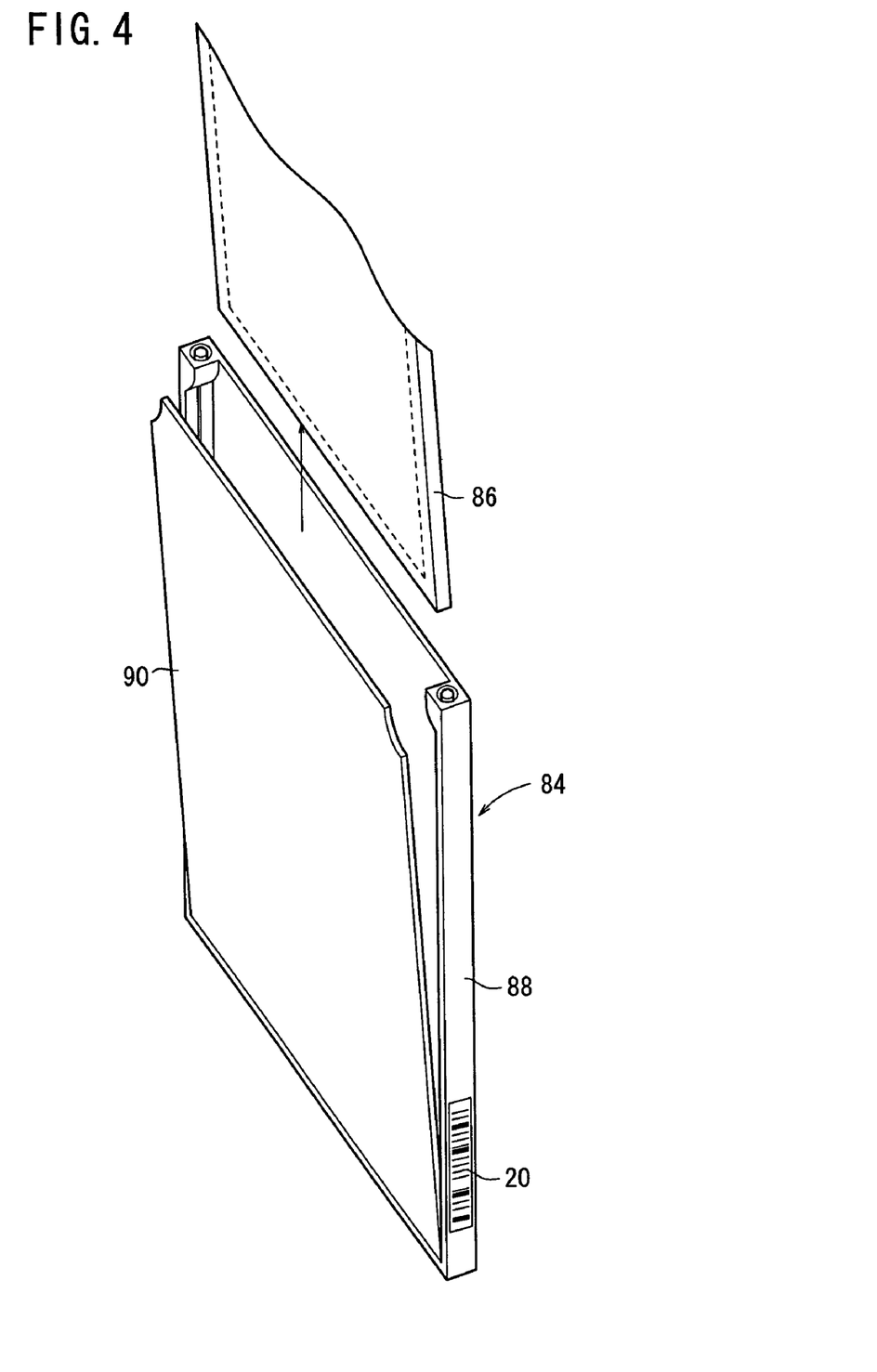
FIG. 4 is a perspective view of another cassette and another stimulable phosphor panel which can be used in the radiation image information reading and erasing apparatus according to the present invention.

FIG. 4 shows a cassette 84 and a stimulable phosphor panel 86 which can also be used in the radiation image information reading and erasing apparatus 10 according to the present invention instead of the cassette 12. As shown in FIG. 4, the cassette 84 has a casing 88 and a lid 90 pivoted to the casing 88, and the stimulable phosphor panel 86 is placed between the casing 88 and the lid 90.

The radiation image information reading and erasing apparatus 10 which uses the cassette 84 and the stimulable phosphor panel 86 operates as follows. After the cassette 84 is delivered from the stock unit 48 to the releasing unit 49, the lid 90 is opened by an unlocking mechanism (not shown), and the stimulable phosphor panel 86 is removed from the cassette 84 by the panel ejecting mechanism 36 and supplied to the reading unit 52. The cassette 84 from which the stimulable phosphor panel 86 has been removed is fed by the holder 50 and the conveyor 60 to the second waiting unit 55 where the cassette 84 waits until it receives the stimulable phosphor panel 86. After remaining radiation image information has been erased from the stimulable phosphor panel 86 by the erasing unit 64, the stimulable phosphor panel 86 is stored back into the cassette 84, which is then delivered to the cassette discharger 40.

Figure 5:
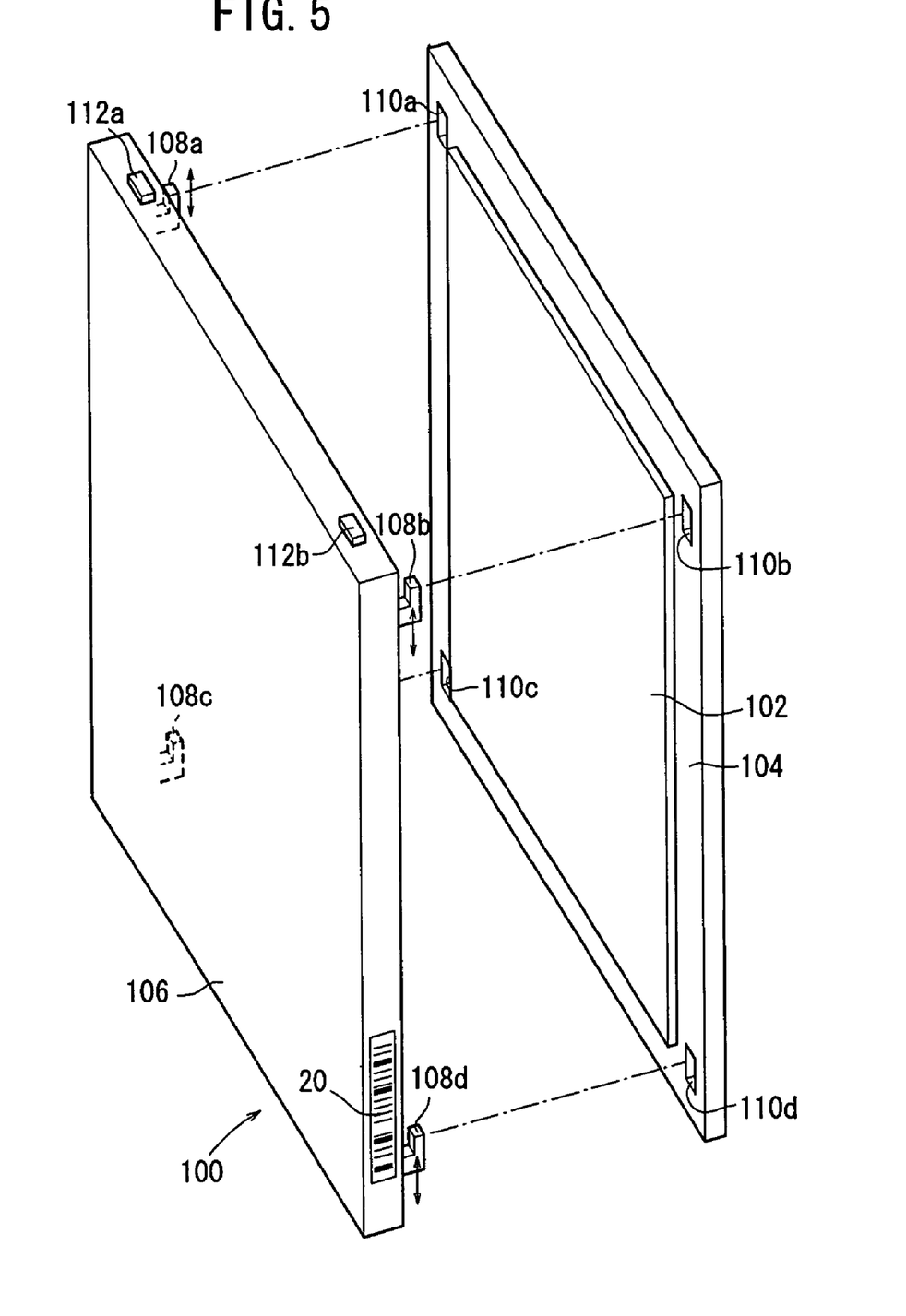
FIG. 5 is an exploded perspective view of still another cassette and still another stimulable phosphor panel which can be used in the radiation image information reading and erasing apparatus according to the present invention.

FIG. 5 shows a cassette 100 and a stimulable phosphor panel 102 which can also be used in the radiation image information reading and erasing apparatus 10 according to the present invention. As shown in FIG. 5, the cassette 100 has a support base 104 for supporting the stimulable phosphor panel 102 thereon and a lid 106 for protecting the stimulable phosphor panel 102. The lid 106 is removably coupled to the support base 104 by a plurality of fingers 108a through 108d engaging in respective slots 110a through 110d defined in the support base 104. The fingers 108a through 108d are movable with respect to the lid 106 in the directions indicated by the arrows, and are coupled to push buttons 112a, 112b disposed on an end face of the lid 106.

The radiation image information reading and erasing apparatus 10 which uses the cassette 100 and the stimulable phosphor panel 102 operates as follows. In the releasing unit 49, the push buttons 112a, 112b are pushed by an unlocking mechanism (not shown) to release the fingers 108a through 108d from the slots 110a through 106. The lid 106 is now detached from the support base 104, and the stimulable phosphor panel 102 is supplied together with the support base 104 to the reading unit 52 by a panel ejecting mechanism (not shown). The lid 106 from which the stimulable phosphor panel 102 has been removed is fed by the holder 50 and the conveyor 60 to the second waiting unit 55 where the lid 106 waits until it is called to receive the stimulable phosphor panel 102. After remaining radiation image information has been erased from the stimulable phosphor panel 102 by the erasing unit 64, the stimulable phosphor panel 102 is combined with the lid 106, whereupon the cassette 100 is delivered to the cassette discharger 40.

Although certain preferred embodiments of the present invention have been shown and described in detail, it should be understood that various changes and modifications may be made therein without departing from the scope of the appended claims.

What is claimed is:

1. An apparatus for reading and erasing radiation image information, comprising:
   a cassette loader for loading a plurality of cassettes each storing therein a stimulable phosphor panel with radiation image information recorded therein;
   a reading unit for applying stimulating light to said stimulable phosphor panel which is removed from one of said plurality of cassettes supplied from said cassette loader to emit light from said stimulable phosphor panel, and photoelectrically reading the light emitted from said stimulable phosphor panel to obtain the radiation image information recorded in said stimulable phosphor panel;
   a first panel supply mechanism for removing said stimulable phosphor panel from said one of said plurality of cassettes and supplying said stimulable phosphor panel to said reading unit;
   an erasing unit for applying erasing light subsequent to obtaining the radiation image information to said stimulable phosphor panel to erase remaining radiation image information therefrom;
   a second panel supply mechanism for removing said stimulable phosphor panel from said erasing unit and supplying said stimulable phosphor panel to said one of said plurality of cassettes; and
   a feed mechanism for individually feeding said plurality of cassettes and said stimulable phosphor panels between said reading unit and said erasing unit,
   a cassette discharger for discharging each of said plurality of cassettes each storing a stimulable phosphor panel therein; and
   an enclosure which encloses the reading unit, the erasing unit, the first panel supply mechanism, the second panel supply mechanism, the feed mechanism and at least two of the plurality of cassettes storing therein stimulable phosphor panels for simultaneous processing,
   wherein said one of said plurality of cassettes from which said stimulable phosphor panel has been supplied to said reading unit is fed by said feed mechanism to said erasing unit so as to wait for said stimulable phosphor panel, said stimulable phosphor panel from which the radiation image information has been read by said reading unit is supplied to said erasing unit by said feed mechanism, and said stimulable phosphor panel from which the remaining radiation image information has been erased by said erasing unit is supplied to said one of said plurality of cassettes which is waiting by said erasing unit.

2. An apparatus according to claim 1, further comprising:
   a waiting unit disposed closely to said erasing unit for keeping said one of said plurality of cassettes from which said stimulable phosphor panel has been removed, waiting for said stimulable phosphor panel.

3. An apparatus according to claim 1, wherein said first panel supply mechanism comprises:
   an unlocking mechanism for unlocking said stimulable phosphor panel from said one of said plurality of cassettes; and
   a panel ejecting mechanism for ejecting the unlocked stimulable phosphor panel from said one of said plurality of cassettes.

4. An apparatus according to claim 1, wherein said reading unit and said erasing unit are shielded against entry of light by respective partition walls.

5. An apparatus according to claim 1, further including isolation walls disposed around said cassette discharger for blocking radiations applied from outside.

6. The apparatus of claim 1, wherein said remaining radiation image information is erased from a first stimulable phosphor panel while a second stimulable phosphor panel is fed between said reading unit and said erasing unit, and said radiation image information is obtained from said second stimulable phosphor panel while said first stimulable phosphor panel is fed between said reading unit and said erasing unit.

7. The apparatus according to claim 1, wherein the reading unit applies stimulating light to the first stimulable phosphor panel concurrently with the erasing unit applying erasing light to the second stimulable phosphor panel.

8. A method of reading and erasing radiation image information, comprising:
   removing a first stimulable phosphor panel from a first one of a plurality of cassettes and supplying said first stimulable phosphor panel to a reading unit;

transporting said first one of said plurality of cassettes from which said first stimulable phosphor panel has been removed to an erasing unit so as to wait for said first stimulable phosphor panel;

reading radiation image information recorded in said first stimulable phosphor panel with said reading unit while a second stimulable phosphor panel is being transported or being erased with said erasing unit;

supplying said first stimulable phosphor panel from which radiation image information has been read by said reading unit to said erasing unit;

erasing remaining radiation image information from said first stimulable phosphor panel with said erasing unit while a third stimulable phosphor panel is being read with said reading unit or is being transported; and storing said first stimulable phosphor panel from which the remaining radiation image information has been erased into said first one of said plurality of cassettes which is waiting by said erasing unit.

9. A method according to claim 8, wherein said step of reading the radiation image information recorded in said second stimulable phosphor panel with said reading unit and said step of erasing the remaining radiation image information from said first stimulable phosphor panel with said erasing unit, are performed concurrently.

10. An apparatus for reading and erasing radiation image information, comprising:

means for loading a plurality of cassettes each storing therein a stimulable phosphor panel with radiation image information recorded therein;

means for removing said stimulable phosphor panel from said one of said plurality of cassettes;

means for reading light emitted from said stimulable phosphor panel to obtain the radiation image information;

means for erasing remaining radiation image information from said stimulable phosphor panel;

means for individually feeding said plurality of cassettes and said stimulable phosphor panels between said means for reading and said means for erasing;

means for enclosing said means for reading, said means for erasing, said means for individually feeding and at least two of said plurality of cassettes storing therein stimulable phosphor panels for simultaneous processing; and means for discharging each of said plurality of cassettes each storing a stimulable phosphor panel therein, wherein said one of said plurality of cassettes from which said stimulable phosphor panel has been supplied to said means for reading is fed by said means for individually feeding to said means for erasing to wait for said stimulable phosphor panel from which the radiation image information has been read and erased to be supplied by said means for erasing to said one of said plurality of cassettes which is waiting.

* * * * *